United States Patent [19]

Stupka et al.

[11] Patent Number: 5,192,309

[45] Date of Patent: Mar. 9, 1993

[54] PROSTHETIC HEART VALVE

[75] Inventors: Jonathan C. Stupka; Jack C. Bokros; Michael R. Emken, all of Austin; Axel D. Haubold, Liberty Hill; T. Scott Peters, Georgetown, all of Tex.

[73] Assignee: Onx, Inc., Austin, Tex.

[21] Appl. No.: 837,761

[22] Filed: Feb. 18, 1992

Related U.S. Application Data

[63] Continuation-in-part of Ser. No. 674,871, Mar. 25, 1991, Pat. No. 5,152,785.

[51] Int. Cl.$^5$ .................................................. A61F 2/24
[52] U.S. Cl. ........................................................... 623/2
[58] Field of Search .......................................... 623/2, 1

[56] References Cited

U.S. PATENT DOCUMENTS

| | | | |
|---|---|---|---|
| 4,178,639 | 12/1979 | Bokros | 623/2 |
| 4,272,854 | 6/1981 | Bokros | 3/1.5 |
| 4,308,624 | 1/1982 | Klawitter | 3/1.5 |
| 4,328,592 | 5/1982 | Klawitter | 3/1.5 |
| 4,373,216 | 2/1983 | Klawitter | 3/1.5 |
| 4,443,894 | 4/1984 | Klawitter | 3/1.5 |
| 4,451,937 | 6/1984 | Klawitter | 3/1.5 |
| 4,692,165 | 9/1987 | Bokros | 623/2 |
| 4,822,353 | 4/1989 | Bokros | 623/2 |
| 4,863,458 | 9/1989 | Bokros | 623/2 |
| 4,872,875 | 10/1989 | Hwang | 623/2 |
| 5,080,669 | 1/1992 | Tascon et al. | 623/2 |

FOREIGN PATENT DOCUMENTS 9101698 2/1991 PCT Int'l Appl. .

Primary Examiner—David Isabella
Assistant Examiner—Dinh X. Nguyen
Attorney, Agent, or Firm—Fitch, Even, Tabin & Flannery

[57] ABSTRACT

Heart valves, particularly those having two identical leaflets, are shown which utilize improved pivot arrangements that create prompt response to flow reversal and minimize impact at the instant of closing. Illustrated are valves having pairs of leaflets that can assume an orientation in the fully open position that is precisely parallel to the centerline of the passageway, yet which will promptly respond upon blood flow reversal and quickly close to prevent substantial regurgitation. The ability of the leaflets to assume a precisely parallel or low energy position in the bloodstream reduces pressure drop across the valve and results in improved flow characteristics. Prompt closing movement pivoting from a parallel position is effected by creating a camming action adjacent the upstream edges of the leaflets while positively guiding the overall path of leaflet translation and rotation by interengagement at other locations spaced from the upstream edges. The pivot arrangements are particularly effective to positively guide the leaflets to assure effective closing movement regardless of momentary deviations in the dynamics of the reverse flow of blood through the valve.

20 Claims, 4 Drawing Sheets

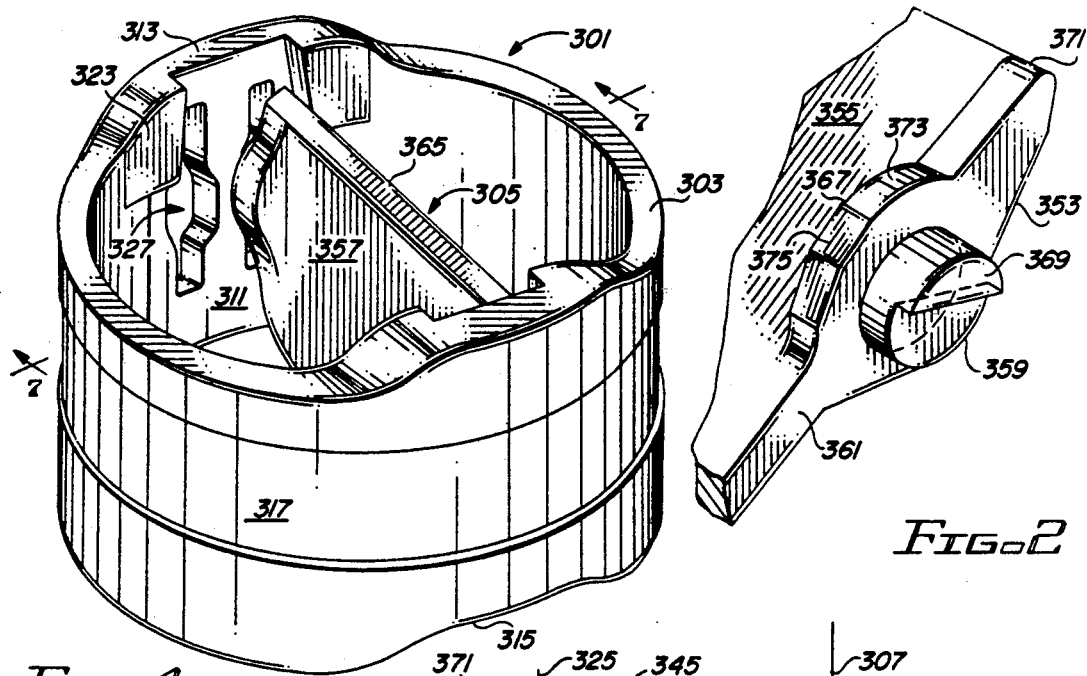
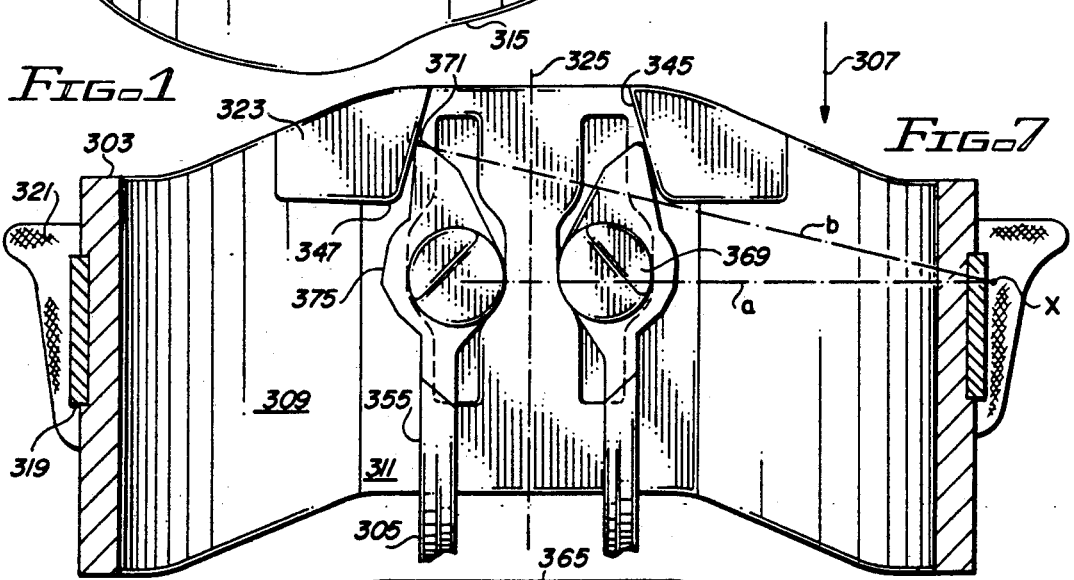
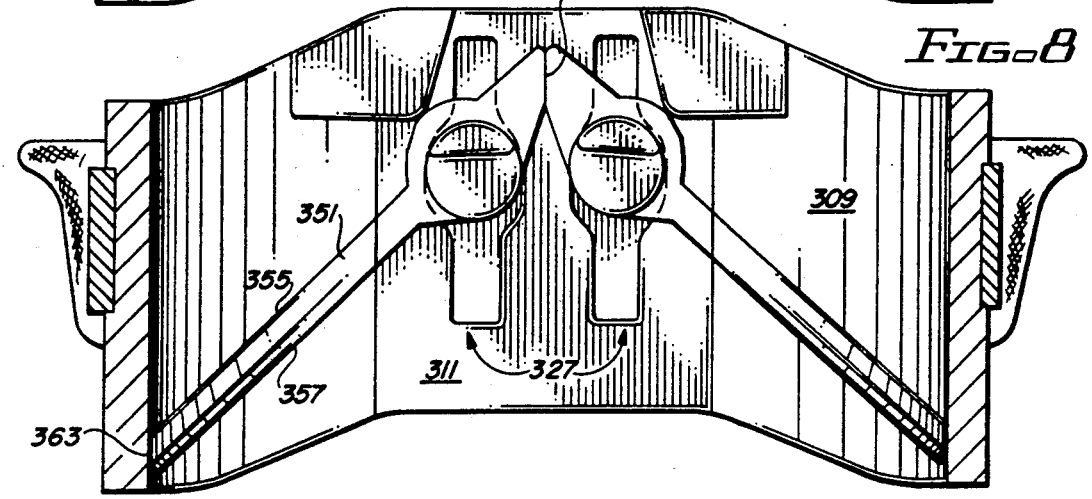

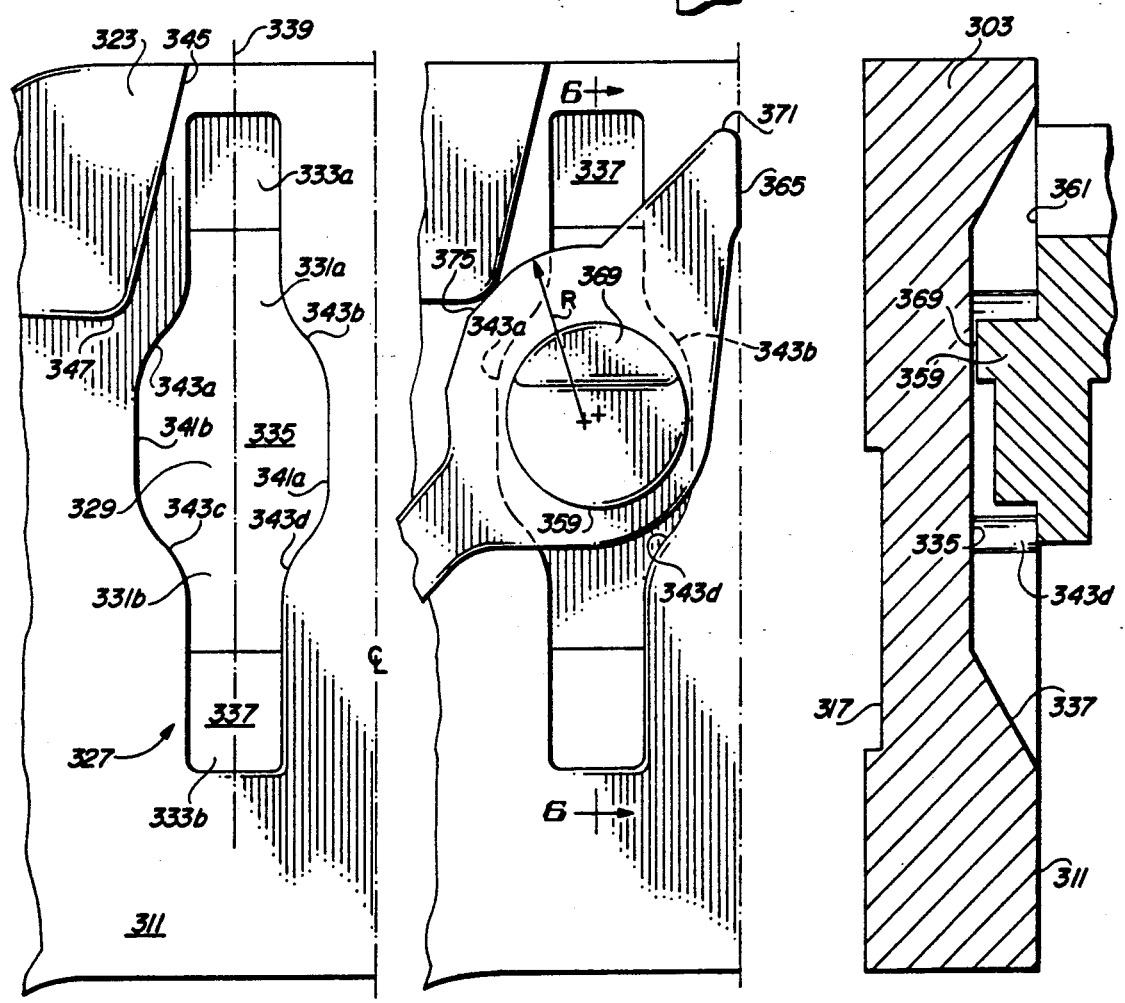

PROSTHETIC HEART VALVE

This application is a continuation-in-part of U.S. application Ser. No. 07/674,871 filed Mar. 25, 1991 now U.S. Pat. No. 5,152,785.

FIELD OF THE INVENTION

The present invention relates to mechanical heart valve prostheses and, in particular, to improved prosthetic heart valves having valve members or occluders which both pivot and translate in moving between the open and closed positions.

BACKGROUND OF THE INVENTION

A wide variety of heart valve prostheses have been developed to operate hemodynamically, in conjunction with the pumping action of the heart, to take the place of defective natural valves. These valves are designed to function with valve members both in the form of a single occluder and a pair of occluders or leaflets, which valve members pivot along an eccentric axis (or both pivot and translate) to open and close a central blood flow passageway through the valve body.

U.S. Pat. No. 4,272,854 (Jun. 16, 1981) shows an early version of a bi-leaflet heart valve having an ear extending from each lateral side of the leaflet which pivots in a recess, guided in part by a knob which travels in a longitudinal slot that is cut more deeply into the sidewall of the valve body.

U.S. Pat. No. 4,373,216 (Feb. 15, 1983) discloses both single occluder and bi-leaflet heart valves wherein protrusions, extending radially inward from the flat sidewall sections of the valve body, guide valve members which have slots in their lateral edges to receive such protrusions.

U.S. Pat. No. 4,308,624 (Jan. 5, 1982) discloses heart valves of the single occluder and bi-leaflet type which have curved valve members which both rotate and translate in moving between the open and closed positions. Although the leaflets are intended to be able to assume a parallel orientation in the open position, as shown in FIG. 3, study of the arrangement shows that, upon reversal of blood flow through the passageway, the leaflets could translate upstream without beginning to rotate toward the closed position. Although pivoting could occur in the intended manner, once the leaflets have moved upstream guided by the path the spherical ears trace in the slots 21, one or both of the leaflets might possibly counterrotate, depending upon the instantaneous attitude of blood flow, and thereby not close on that stroke. U.S. Pat. No. 4,443,894 (Apr. 24, 1984) discloses a later version of this general type valve and illustrates an embodiment wherein the leaflets in their open position are angled relative to the centerline plane (see Column 4, lines 39–43) so that, when flow reversal occurs (as depicted in FIG. 4), the alignment of angled surfaces 44 of the stops 41 and their placement is such that there can be no inward pivoting or counterrotation of the leaflets (see Column 5, lines 34–41).

U.S. Pat. No. 4,451,937 (Jun. 5, 1984) shows additional single occluder and bi-leaflet valves wherein valve members, arranged at an angle to the centerline plane in the open position, pivot and translate to a closed position guided, in part, by laterally extending ears 21 which move in generally arcuate slots or depressions 23.

U.S. Pat. No. 4,328,592 shows other alternative embodiments of heart valves of this general type including some which have elongated slots in the valve sidewall with grooves to permit controlled leakage.

U.S. Pat. No. 4,692,165 (Sep. 8, 1987) discloses single occluder and bi-leaflet valves wherein valve members are guided in pivotal and translational movement in part by notches in their lateral edges which receive arcuate posts protruding from flat sidewall sections of the valve body.

U.S. Pat. No. 4,863,458 (Sep. 5, 1989) discloses bi-leaflet heart valves having leaflets of varying thickness which are guided in translational and pivotal movement by laterally extending ears that are received in recesses formed in the flat sidewall sections of the valve bodies.

Commercially developed heart valves using valve members of this type, as generally exemplified by the last 3 U.S. patents mentioned above, have employed valve members which are oriented at an angle to the centerline plane in the open position, so that the backflow of blood will preferentially impinge upon the outflow surfaces of each valve member and thus tend to initially impart a pivotal component to its movement toward closing. It is now felt to be particularly important that a mechanical heart valve prosthesis should provide a passageway through which blood flows freely with a minimum of drag in the open position and, to accomplish such end, that the valve members should be able to assume an orientation which is parallel to the longitudinal axis of the passageway; however, in this orientation, they should be highly responsive so as to close quickly upon the occurrence of backflow. Improvements in construction to create mechanical valves having such characteristics have continued to be sought.

SUMMARY OF THE INVENTION

The present invention provides mechanical heart valve prostheses having the aforementioned desirable characteristics wherein a valve member or members can assume an open position parallel to the longitudinal axis of the valve passageway, but which will promptly translate and begin to pivot toward its closed position orientation as soon as upstream displacement of the valve member or occluder occurs within the valve body. These valves include a pivot arrangement wherein a projection, extending inward from the valve body interior wall, is located so as to generally extend upstream of the valve member when it is in its open position. The projection is slidingly engaged by the valve member when upstream displacement occurs. As a result of such engagement, upstream displacement of the valve member upon blood flow reversal immediately results in a camming action that causes a positive pivoting moment to be applied to the valve member; this assures that the valve member, even if it should be in an open position orientation precisely parallel to the valve centerline, will promptly begin to pivot or swing toward its closed position orientation.

By preferably locating the projection so that the sliding, camming contact occurs at the upstream tip of the valve member, the moment arm is maximized, contributing to efficient, positive closing action. To assure the desired positive action is created, additional interengaging elements are also provided both on the valve body and on the valve member, at a location apart from where such camming contact would occur, which, in cooperation with the camming engagement against the projection, guarantee that the desired pivoting movement of the valve member promptly occurs and continues throughout the desired path. Other features of the valve pivot arrangement create a generally soft, final closing movement and distribute load on the valve member at the instant of closing such as to avoid concentration of load at specific points that might result in high incidence of wear.

BRIEF DESCRIPTION OF THE DRAWINGS

FIG. 1 is a perspective view of a bi-leaflet heart valve embodying various features of the present invention, shown with the left hand leaflet removed and with the right hand leaflet in the open position;

FIG. 2 is an enlarged fragmentary view, shown in perspective, of the leaflet from the heart valve of FIG. 1;

FIG. 3 is a fragmentary plan view partially in section of the bi-leaflet heart valve shown in FIG. 1 with the left hand leaflet removed and with the right hand leaflet shown in its open position;

FIG. 4 is an enlarged fragmentary view showing the elongated slot in the sidewall of the valve body and the adjacent projection;

FIG. 5 is a view similar to FIG. 4 showing the leaflet within the slot in the location where it would reside when the leaflets are both in the fully closed positions;

FIG. 6 is a sectional view taken generally along the line 6—6 of FIG. 5;

FIG. 7 is an enlarged cross sectional view of the heart valve, taken generally along the line of 7—7 of FIG. 1, showing both leaflets in elevation, installed and in the open position;

FIG. 8 is a cross sectional view similar to FIG. 7 showing the two leaflets in elevation and in the closed position;

DETAILED DESCRIPTION OF THE PREFERRED EMBODIMENTS

Figure 9:
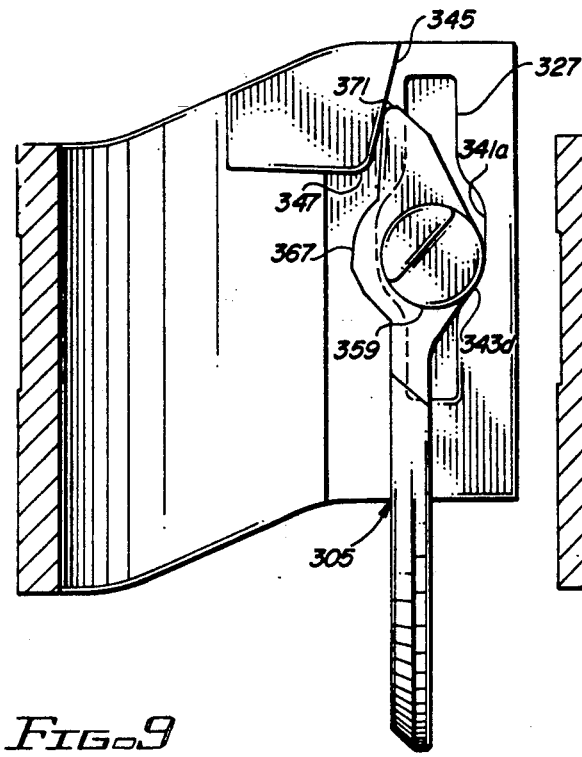
FIGS. 9, 10, 11 and 12 are fragmentary sectional views showing the left hand leaflet as it may move in translating and rotating from the fully open position (FIG. 9) to the fully closed position (FIG. 12)

Shown in FIGS. 1 to 12 of the drawings is a preferred embodiment of a prosthetic heart valve 301 constructed so as to embody various features of the present invention. The heart valve 301 is of a bi-leaflet construction; however, it should be understood that the principles of the present invention can be incorporated into a heart valve having a single valve member or occluder as generally shown and described in pending U.S. patent application Ser. No. 674,871, filed Mar. 25, 1991, the disclosure of which is incorporated herein by reference.

Very generally, these heart valves have improved flow characteristics, particularly when the valve is in the fully open position. Because the occluders can align substantially parallel to the valve centerline in the open position, or can align at slight deviations thereto depending upon local variations in blood flow path through the valve at any instant, they minimize drag and substantially reduce boundary layer separation along the major surfaces of the occluders. The valve design also provides good washing characteristics to prevent stagnation and potential clotting. Furthermore, heart valves of this design exhibit a rapid response to the change in direction of blood both in respect of opening and closing. Still further, in valves of this design, there is relatively low impact of the occluders against the valve body at the time of closing, thus reducing hemolysis or similar injury to blood cells and also eliminating potential problems with the creation of regions of substantial wear.

Heart valve 301 includes a generally annular valve body 303 which carries a pair of pivoting occluders or leaflets 305 that open and close to allow the flow of blood in the downstream direction as indicated by the arrow 307 in FIG. 7 and to prevent any substantial backflow of blood. The valve body 303 defines a blood flow passageway in the form of its generally cylindrical interior surface 309 which is interrupted by a pair of diametrically opposed flat wall sections 311. A pivot arrangement for defining the opening and closing movements of the leaflets 305 includes elements formed on the valve body 303 in the region of these flat wall sections 311, which elements coact with corresponding elements formed as a part of each of the leaflets.

The valve body 303 preferably has a scalloped design, and it is of relatively uniform longitudinal length along its entire circumference. Moreover, this length is preferably equal to at least about 45 percent, and more preferably at least about 60 percent, of the interior diameter of the passageway through the valve body. As best seen in FIGS. 1 and 7, the scalloping is such that the valve body 303 protrudes or bulges with upstream extensions 313 generally in the region of each flat wall section 311 and also has recesses 315 of substantially complementary shape along its downstream edge in the region of the flat wall sections, so as to maintain this preferred minimum length which is most preferably about constant around its entire circumference. The outer surface of the valve body is preferably formed with a shallow groove or channel 317 which receives a metal stiffening ring 319 that adds to the stability and rigidity of the valve body, which is otherwise preferably made of a material having some resiliency, such as pyrocarbon or pyrocarbon-coated graphite as well known in this art. Moreover, the stiffening ring 319 is used to support a sewing ring 321 of an appropriate design (see FIGS. 7 and 8) as is well known in this art. Examples of sewing or suture rings which could be employed are described in U.S. Pat. Nos. 4,535,483 and 3,691,567.

To create the pivot arrangement, the valve body 303 has four upstream projections 323 formed therein which protrude generally radially inward from the interior surface of the valve body and are arranged so that pairs of these projections generally flank the upstream ends of the two diametrically opposed flat wall sections 311 of the valve body. The passageway through the valve body is thus generally circular in cross section except for the two flat wall sections 311, and the centerline of this otherwise circular passageway is indicated by the reference numeral 325 in FIG. 7. An imaginary plane which includes the centerline 325 and which is perpendicular to the two flat wall sections 311 is referred to hereinafter as the centerline plane and is used for reference purposes throughout this specification and claims. In addition to the projections 323, the pivot arrangement includes a pair of depressions in the form of grooves or slots 327 formed in each of the flat wall sections 311 and arranged so that one lies on each side of the centerline plane. As best seen perhaps in FIG. 4, each of the slots has a central section 329 of constant width and constant depth and has upstream and downstream transition sections 331a and b, which narrow in width but remain of constant depth and which in turn lead to upstream and downstream terminal sections 333a and b. The width of the terminal sections 333 is between about 30 and about 60 percent of the width of the central section 329 and preferably between about 35 percent and about 50 percent. As best seen in FIG. 6, the base wall 335 of the slot central section 329 is flat and parallel to the flat wall sections 311 of the valve body interior sidewall. The flat base wall extends through the transition sections 331 of the slots, and then a pair of oblique walls 337 form the bases of the two terminal sections of each slot.

In this embodiment of the heart valve 301, the central section and the remainder of each slot 327 is formed symmetrically about a slot centerline which is indicated in FIG. 4 by the reference numeral 339. In another embodiment of the invention described hereinafter, the central sections of the slots are nonsymmetrical, being further offset from the centerline in a direction away from the centerline plane for a purpose to be explained hereinafter. The central sections 329 are formed with a pair of parallel flat sidewalls 341a and b which are preferably perpendicular to the base wall 335 and to the flat sidewall sections 311 of the valve body. In the transition sections 331, the slot sidewalls curve smoothly inward so as to narrow to the slot to a width equal to that of the terminal section, and these terminal sections are defined by curved wall sections which are indicated in FIG. 4 by the reference numerals 343a, b, c, and d.

The upstream projections 323, as best seen perhaps in FIGS. 3, 4 and 5, are each formed with a camming surface 345 which faces the centerline plane and is oriented at an angle of between about 5° and about 35° to the centerline plane, and preferably at an angle of between about 15° and about 30°. The downstream edge of this camming surface is rounded and preferably leads to an undersurface that is perpendicular to the centerline, although the undersurface itself is not functional. The interior surface 349 of each projection is also generally flat, as best seen in FIG. 3, and blends smoothly into the cylindrical sidewall 309 along its outer edge; however, if desired, it can be cut away along its upstream edge to provide a more streamlined flow of blood through the valve 301.

The leaflets 305 are preferably identical in shape and form; they have a generally flat main body section 351, preferably of substantially constant thickness, and have a pair of side sections 353 of greater thickness wherein the cooperating elements of the pivot arrangement are formed. Although the main body sections 351 of each leaflet are preferably flat, other configurations, such as cylindrical sections, can alternatively be employed as discussed in more detail in copending U.S. application Ser. No. 674,871. The flat main body sections of each leaflet are defined by an inflow surface 355 and an outflow surface 357 which are parallel to each other, and as best seen in FIG. 8, the inflow surface is the surface which faces upstream in the closed position whereas the outflow surface faces downstream. In addition to the thickened regions which constitute the side sections 353, each leaflet has a pair of arcuate ears or pegs 359 which extend laterally outward from the otherwise flat, lateral edge surfaces 361 of the side sections; the pegs 359 are received in the slots 327 and coact therewithin as a part of the pivot arrangement. The pegs are coaxial, and the axis is offset from the central plane through the flat leaflet body 351.

The leaflets 305 each have a major arcuate edge surface 363 which is located at the downstream edge of the leaflet in the open position and a minor mating edge surface 365 which is located at the opposite, upstream edge of the leaflet in the open position. The arcuate edge surface 363 preferably has a configuration such as to abut and seat against the cylindrical sidewall of the valve body in the closed position. The minor edge surface 365 is preferably flat and formed at an angle so as to mate flush against the corresponding mating edge surface of the opposing leaflet, as best seen in FIG. 8, and the minor edge surface is accordingly oriented at an angle to the main body section which is substantially the same as the downstream angle which the outflow surface 357 of the body section 351 of the leaflet forms with the centerline plane in the closed position, i.e. preferably an angle between about 30° to 60°. The angle in question defines the amount of angular rotation that each leaflet must undergo in moving from the fully open to the fully closed position inasmuch as the leaflets can assume the precisely parallel open position orientation. As a result, there may be advantages in having a smaller angle insofar as the leaflets need not rotate as great an angular distance in order to reach the fully closed position. Thus, this feature is taken into consideration in designing a valve, and in the illustrated embodiment, the angle is about 45°.

In addition to the major arcuate edge surface 363 and the minor mating edge surface 365, each leaflet includes a pair of the essentially flat lateral edge surfaces 361 which form the edges generally in the regions of the thicker side sections and from which the arcuate ears or pegs 359 protrude. These lateral edge surfaces 361 are preferably flat, and the leaflets 305 are proportioned so that there is minimal clearance between the flat wall sections 311 of the valve body and the flat lateral edge surfaces of the leaflets. This clearance is sufficient to enable the leaflets to freely pivot and to allow controlled leakage of blood through this slight gap when the leaflets are in the closed position, as generally known in this art. During pivoting movement, the lateral edge surfaces 361 will move closely adjacent the flat wall sections 311 of the valve body, one of which wall sections usually serves as a bearing surface for the pivoting leaflet.

The portions of the thickened side sections 353 of the leaflet that extend from the inflow surface 355 are formed with camming elements 367 which, as explained hereinafter, bear against the rounded downstream edges 347 of the projections and serve to define the closing movement of each of the leaflets. As best seen in FIGS. 2 and 7, the arcuate ears or pegs 359 which protrude laterally from the side sections 353 are preferably in the form of short right circular cylinders that are received within the central portions 329 of the slots and that have diameters such that there can be clearance along both edges as can be seen from FIG. 5. The diameter of such cylinders is preferably less than the axial length of height thereof, and the width of the central portion 329 of the slots 327 is preferably not more than about 10 percent greater than the diameter of the pegs 359. The outer ends of the peg 359 are preferably reduced in size so that the outer end surface 369 of each peg has the shape of a sector of a circle. The purpose of this size reduction is to provide a controlled leak path that will assure the desired amount of cleansing flow in this region explained in more detail hereinafter.

The edge 371 of each leaflet at the upstream tip thereof, i.e. the junction between the minor mating edge 365 and the inflow surface 355, is rounded, and it constitutes the leading upstream edge of each leaflet in the closing movement thereof. It is this rounded edge 371 that coacts with the camming surfaces 345 on the pair of generally diametrically opposed projections 323, as explained in detail hereinafter, to initiate the closing pivoting movement of each leaflet.

The leaflets are installed in the valve body 303 by squeezing the body at diametrically opposite locations, as for example, along the reference line 7—7 of FIG. 1. The squeezing causes the diametrically opposed flat wall sections 311 to separate a sufficient distance farther from each other to allow the leaflets to be fitted into the interior passageway, with the laterally protruding pegs 359 being received in the respective slots. When the squeezing force is removed, the valve body 303 returns to its original annular configuration, leaving only the desired minimal clearance between the flat wall sections 311 of the valve body and the flat lateral edge surfaces 361 of the leaflets, in which position the leaflets are slidably-pivotally mounted for travel between the closed and open positions. The metal stabilizing ring 319 can be appropriately installed, as by shrink-fitting, following the installation of the leaflets; however, it may be preferred to install the metal stabilizing ring before installing the leaflets. The compressive force applied by the ring 319 can improve the structural properties of a pyrocarbon valve body, pyrocarbon being the preferred material of the construction, and the metal ring 319 has sufficient resiliency to return to its perfectly annular shape following removal of the squeezing force.

When the heart valve is installed in a patient, the two leaflets can assume the orientation illustrated in FIG. 7 wherein the major body portions 351 of both leaflets are precisely parallel to the centerline plane, assuming this is the "low energy" or equilibrium position; thus, they provide very low obstruction to the downstream flow of blood. Yet, despite such a precisely parallel open position, the present construction is such that closing movement of the leaflets begins immediately as flow reversal occurs. The leaflets are preferably mounted so as to, in the open position, divide the valve body passageway into three sections, a center section located between the two leaflets and two flanking sections, the cross sectional area of each of said flanking sections preferably being at least as large as the cross sectional area of said center section.

As best seen in FIGS. 7 and 9, when the leaflets are in the precisely parallel open position, the laterally extending pegs 359 are located at the downstream ends of the central portions 329 of the slots, and the rounded leading edge 371 of each leaflet is in contact with the camming surface 345 of the respective generally diametrically opposite projections. Depending upon tolerances, the actual contact between the right circular cylindrical surface of the peg 359 is with one or both of the curved sidewalls 343c, d that form the downstream transition section of the slot. In the embodiment illustrated in FIG. 9, the relative locations of the slots 327 and the projection camming surface 345 are such that contact occurs only between the surface of each peg and the curved sidewall 343d closer to the centerline plane.

Figure 10:
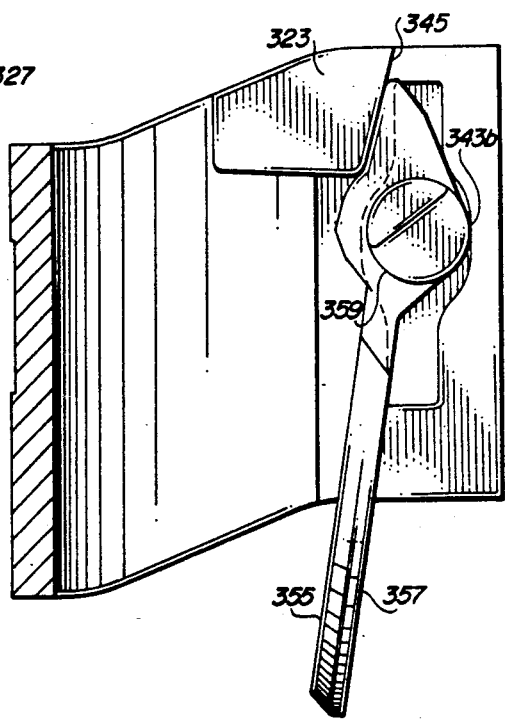

Upon the reversal of blood flow as a result of the contraction of the heart, the backflow of blood in an upstream direction (i.e. upward with respect to FIG. 7) displaces the leaflets upward. The path of their upward movement is defined by simultaneous engagement of the rounded leading edge 371 against the camming surfaces 345 and, at a substantial distance downstream therefrom, of the cylindrical pegs 359 against the flat sidewall 341a of the slot central portion, i.e. the sidewall closest to the centerline plane which faces away therefrom. As a result of the upstream edge being forced to follow this path of movement, the leaflet must begin to pivot or rotate from the parallel orientation shown in FIG. 9 toward its closed position, and comparison of FIGS. 9 and 10 shows that this left-hand leaflet has rotated clockwise as a result of its upward displacement. In this fully translated position, the inflow surface region of the side sections 353 lying just downstream from the leading rounded edge 371 lies in juxtaposition with the camming surface 345, and the right circular cylindrical surfaces of the pegs 359 each bear against the curved sidewall 343b of the upstream transition section of the slot.

Figure 11:
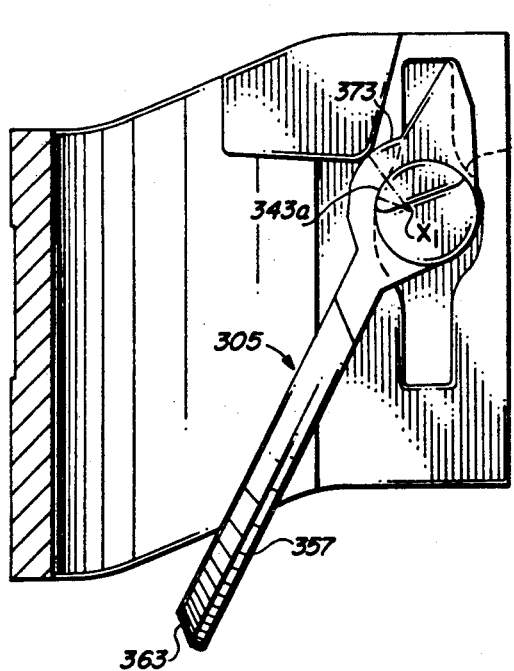

Because this prompt rotation has exposed the outflow surface 357 of the leaflet to more and more of the full force of the backflowing stream of blood, the rotative force vector being applied against each leaflet is amplified. Illustrated in FIG. 11 is a position where rotation has continued and the arcuate surface sections 373 of the camming elements 367 of both side sections are now in engagement with the rounded downstream edges 347 of the pair of projections. As a result, in the illustrated embodiment, the force of the flowing bloodstream has generally caused the cylindrical surface of the peg 359 to now bear against the curved sidewall 343a of the transition section and to lose contact with the curved wall section 343b closer to the centerline plane; however, this is subject to the dynamic conditions within the bloodstream at the moment. If external forces upon the patient or dynamic forces within the bloodstream are different, other intermediate positions could be reached.

Figure 12:
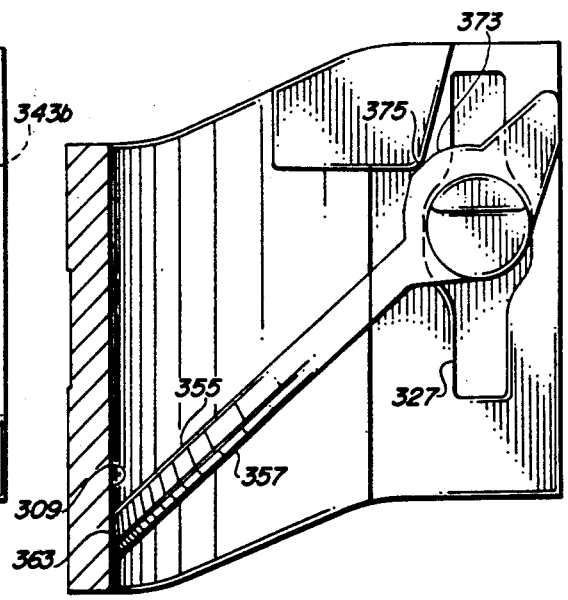

The last phase of the closing movement occurs when rotation has proceeded to the extent that a rear, flat camming section 375 (see FIG. 5) of each of the camming elements 367 of the side sections 353 has come into contact with the rounded downstream edges of the pair of projections. As best seen in FIG. 5, the radius of curvature R of the arcuate camming section 373 is offset slightly from the center of the right circular cylindrical peg 359 so that, as the rotation from the orientation generally shown in FIG. 10 occurs, the distance constantly increases from the center of the peg to the point on the surface of the camming element 367 in contact with the downstream edge of the projection so that contact with the curved sidewalls 343a of the slot is lost sometime as rotation continues, depending upon the dynamics of the bloodstream at the moment. The proportioning is such that, as shown in FIGS. 5 and 12, contact between the cylindrical surface of the peg 359 and the curved sidewall 343a that defines the upstream transition section must be lost before the major arcuate edge 363 seats against the interior cylindrical surface 309. Moreover, abutment of the two mating edge surfaces 365 of the leaflets assures that there is no contact between the surface of the peg 359 and the curved sidewall 343b closest to the centerline plane. As a result, this arrangement removes all of the load from the laterally extending pegs 359 at the moment of final closing movement which positively relieves potential wear in these regions and provides for a relatively soft closure. The length of the central sections 329 of the slots is preferably such that the straight line translation of the peg is not greater than a distance equal to about 50 percent of the diameter of the cylinder.

As been seen in FIGS. 3, 5 and 6, in the fully closed position, there is a controlled leakage path from the high pressure below (i.e. downstream of) the closed leaflets throughout the region of the pivot arrangement. More specifically, as can be seen in FIGS. 3 and 5, high pressure blood fills the lower portions of the slots 327, and controlled backflow is allowed along the straight sidewalls 341a, b of the central section 329 past the cylindrical surface of the pegs, which assures washing occurring at these locations. Moreover, as can be seen from FIGS. 3 and 6, the proportioning of the pegs is such that even when the lateral edge surface 361 of one of the leaflets is in contact with the respective flat sidewall section 311 of the valve body, there is a slight clearance between the base wall 335 of the slot and the edge surface 369 of the peg. Accordingly, there will also be a backflow of blood through this region. The amount of this backflow is controlled by adjusting the length of the flow path through the narrow region, as best seen in FIG. 6, by appropriately proportioning the reduction in size of the end of the peg 359 to either increase or decrease the area of end surface 369 which is in the form of the circular sector as best seen in FIGS. 2 and 5. In the illustrated embodiment, the leaflets, in the closed position, are oriented (i.e. have an angle of repose) at an angle of about 45° to the centerline plane; this angle is most preferably between about 40° and about 50°.

When the next pumping cycle of the heart occurs, so that there is again a flow of blood in the normal downstream direction through the valve 301, the force of blood on the inflow surfaces 355 of the leaflets causes their immediate displacement downward. Because of the eccentric axes upon which the leaflets 305 are mounted, there is also an immediate pivoting motion that occurs. The leaflets quickly reach the downstream transition region in the slots 327, and in this position, the cylindrical surfaces of the laterally extending pegs 359 bear against the curved sidewall surfaces 343c, d. Thereafter, essentially pure rotation occurs until the rounded leading edge 371 of the leaflet contacts the camming surface 345 of the projection, as shown in FIG. 9. This occurs an instant before the leaflet reaches its full open, i.e. parallel to the centerline, orientation, and the preferred location of the slot 327 is such that the leaflet is displaced just slightly toward the centerline plane so that the laterally extending pegs 359 are thereafter only in contact at about the junction between the flat sidewall 341a of the central section of the slot and the curved sidewall 343d. This position is preferred because, with the pegs 359 in contact with the sidewall 341a of the slot nearest the centerline plane, upward displacement at the beginning of backflow immediately results in the beginning of pivoting motion as can be seen by comparing FIG. 10 with FIG. 9.

A particularly advantageous pivot arrangement is thus created by the deployment of projections which cause pivoting closing movement to begin as a result of contact with the rounded leading upstream edges 371 of the leaflets. When the closing movement first begins, there is a prompt and rapid rotation of the leaflets about a center of rotation of pivot (CRP) that is initially spaced a significant distance beyond the outflow surface 357 of the leaflet, preferably at least a distance equal to one-half the radius of the valve passageway. The term "CRP" is used to describe the theoretical instantaneous pivot center about which rotation of the leaflet is occurring at any instant in its movement from the open position to the closed position. Where there is contact with the valve body at two spaced apart locations generally along each lateral edge of the leaflet, i.e. (a) with the generally radially extending projections 323 and (b) with the sidewall of the slot 327, the CRP is determined by constructing perpendiculars to the respective supporting surfaces of the valve body at the precise points where such contact occurs and then determining the point where these perpendiculars cross. For example, assuming FIG. 7 illustrates the position of the leaflet as translation and rotation are just beginning, the CRP for the left hand leaflet would be at point X which lies at the intersection of the line (a) that is perpendicular to the flat sidewall 341a of the central section 329 of the slot and passes through the center or axis of the cylindrical peg 359 and the line (b) that is normal to the camming surface 345 at the point of its contact with the rounded leading edge 371 of the leaflet. These lines a and b and the intersection X are shown in FIG. 7. As a result, there is a very large initial effective torque which drives the leaflet in its rotational movement, achieving a prompt response to cause the leaflet to begin to move toward its closed position and minimizing the overall regurgitation of blood. Moreover, the location of the point of contact along the leading upstream edge of the leaflet increases the size of the moment arm which is contributing to the prompt initial opening movement of the leaflets.

In addition, a further significant advantage is found in this type of pivot construction because the CRP, during closing movement, shifts from its initial location (which as can be seen from FIG. 7, is not only well beyond the outflow surface 357 of the leaflet, but also beyond the centerline plane for the bi-leaflet valve) to a location near the outflow surface of the leaflet or even within the body of the leaflet when the leaflets near the end of their closing rotation. The change in location of the CRP during closing movement can be seen by examination of the embodiment illustrated in FIG. 11 where the point of intersection is labeled as the point $X_1$ and is located within the plane of the leaflet. As a result of this change in CRP location, there is a lessening of the rotational moment arm and a consequent softening of the final impact of the leaflet against the valve sidewall, thereby reducing both noise and wear.

The design is preferably such that there are two sets of force vectors supporting the leaflets in the fully closed position. One is at the points of contact between the interior cylindrical sidewall 309 of the valve body and the major arcuate edge 363 of the leaflet, and the other set is along the lines of contact between the rounded downstream edges 347 of the pair of projections and the respective rear flat sections 375 of the camming elements The intersections of the composite vectors representative of these two sets of vectors when projected into a common plane parallel to the flat wall sections 311 can be adjusted as desired by adjusting the angle of the flat camming surface 375 in relationship to the plane of the inflow surface 355 of the leaflets. These considerations are explained in detail in copending U.S. patent application Ser. No. 674,871, and they are used to achieve the desired tight closing contact between the mating edge surfaces 365 of the leaflets which positively guards against undesired regurgitation leakage.

Overall, the illustrated embodiment, wherein there is contact between leading edge portions of each leaflet with the camming surfaces 345 of the projections along both lateral edges thereof and wherein there is also confinement of the laterally extending pegs 359 within the slots to thereby create coaction between the interengaging sidewalls of the slots 327 and the right circular cylindrical surfaces of the pegs, assures that precise control of the path of leaflet movement is maintained throughout the entire closing movement. The different dynamic conditions that occur within the bloodstream and that could potentially cause aberrations in occluder movement have more recently been taken into consideration in heart valve design, and it has been found that the combinations of interengaging elements illustrated in this patent application are particularly effective in assuring that the desired closing will occur regardless of such momentary aberrations.

Figure 13:
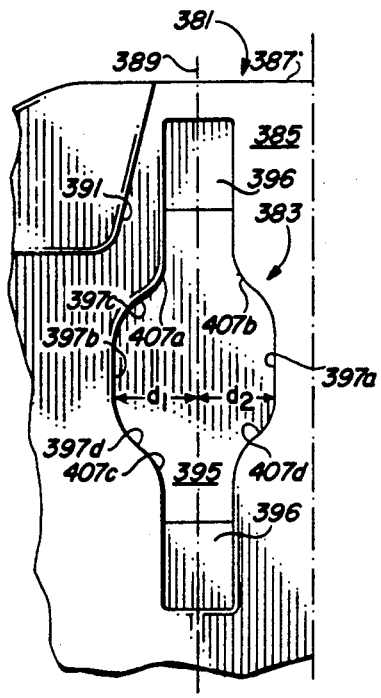
FIG. 13 is a view, similar to FIG. 4, showing a fragment of an alternative embodiment of a heart valve body embodying various features of the invention, which has asymmetric slots provided in the interior sidewalls.

Illustrated in FIGS. 13 through 17 are fragmentary views of an alternative prosthetic heart valve 381 also embodying various features of the invention. Inasmuch as there are substantial similarities between the valve 381 and heart valve 301 previously described in detail, the description of the alternative embodiment will concentrate on the differences between the two valves, and it should be understood that those features not specifically mentioned are essentially similar. One difference between the two valves lies in the fact that, in the valve 381, grooves or slots 383 are formed in flat sidewall sections 385 of a valve body 387 in a manner so as to be asymmetric about a slot axial centerline 389. The location of the asymmetric slots 383 relative to camming surfaces 391 of projections 393 is adjusted to achieve the pattern of contact described hereinafter. The lack of slot symmetry is the result of the central portion 395 of the slot instead of being symmetrical about the axial centerline, which is defined by the upstream and downstream terminal sections 396, is created so that it is wider on the side away from the valve body centerline plane, as best seen in FIG. 13. In other words, the flat sidewall section 397b of the central portion of the slot, lying farther away from (and facing toward) the centerline plane of the valve body, is spaced distance $d_1$ from the centerline 389 of the slot which is greater than distance $d_2$ that represents the spacing of the flat sidewall section 397a that lies closer to the centerline plane. The width of the terminal sections 396 are about 35% of the width of the central portion of the slot 383. As a result of the greater offset of the flat sidewall 397b, there are preferably created short, oblique, flat sidewall sections 397c and 397d which flank the sidewall 397b, being spaced therefrom by short arcuate sidewall sections. In addition, thickened arcuate elements 399 of the side sections of the leaflets 401 are not used to cam against the rounded downstream edge surfaces of the projections 393 in guiding the closing movement; instead, once rotation of the leaflet 401 progresses to the extent that the upstream rounded tips 403 are no longer in contact with the camming surfaces 391 of the projections, further closing movement is essentially guided by the interengagement between the cylindrical surfaces of the pair of laterally extending pegs 405 and the cooperating sidewall surfaces of the slots 383. The axes of the pegs 405 are similarly offset from the central plane of the flat body of the leaflets.

More specifically, FIGS. 14 through 17 are views similar to FIGS. 9 through 12 and point up differences between the valve 381 and the valve 301. However, except for the precise location and the asymmetric shape of the slots 383, the valve body 387 is essentially the same as the valve body 303 for the valve 301. The pairs of slots 383 are likewise located in diametrically opposed flat sections 385 of the interior surface of the valve body.

Figure 14:
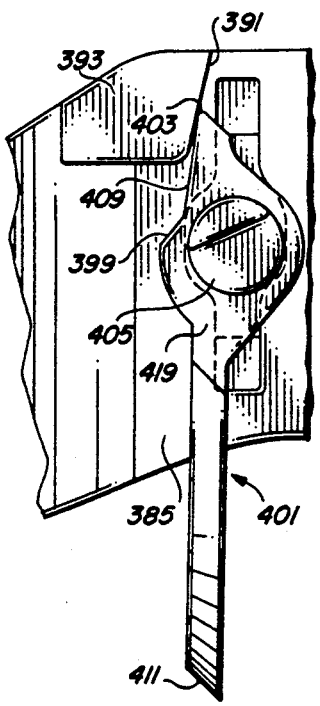
FIG. 14 is a view similar to FIG. 9 of a heart valve showing the left hand leaflet in the full open position in the valve body employing the asymmetric slots shown in FIG. 13.

FIG. 14 shows the left hand leaflet in its open position. With the leaflets 401 in this position, the pivot arrangement is functionally about the same as that supporting the leaflets in the 301 valve. There is contact between the upper leading edge 403 of each leaflet and the camming surfaces 391 on the pair of generally radially inwardly extending protrusions 393, and there is contact between the pegs 405 and the downstream portion of the slot sidewall 397a at the curved sidewall 407d, which is one of the four sidewall sections 407a, b, c, d that define the two transition sections. Depending on the manufacturing tolerances that are allowed, the surface of the pegs 405 could approach the curved sidewall section 407c and could contact it if momentary blood flow patterns were such as to promote a slightly non-parallel alignment of this leaflet.

As the reverse flow of blood begins, the leaflets 401 translate upstream with the pegs 405 of the leaflet likely initially sliding along the flat wall 397a of the central portion of the slot nearest the centerline plane which faces away therefrom. As in the case of the valve 301 described earlier, this causes a rotative force to be applied to the upstream edges 403 of the leaflets, as a result of the interengagement of the rounded upstream edges bearing against the pair of generally diametrically opposed, inwardly extending protrusions and as a result of the interengaging contact, at a downstream location a substantial distance therefrom, between the flat sidewall 397a of the slot and the peg 405, which force acts through a long moment arm and promptly causes initial pivoting of the leaflet toward the closed position orientation. However, the force of the backflow of blood against the outflow surface 408 is expected to eventually displace the leaflet 401 so that the pegs 405 will be in contact with the flat sidewall 397b following completion of translation of the right hand leaflet shown in FIG. 15.

In this embodiment, the thickened side sections 399 at the lateral edges of each leaflet are reduced in height, and the inflow surface regions thereof are not employed to engage the rounded downstream edge of the projections 393 and assist in determining the path of closing movement. Instead, the upstream translating movement of each leaflet 401 is arrested by engagement of the laterally extending pegs 405 against the oblique wall sections 397c of the slots 383. The neck of the asymmetric slot 383 is elongated on the side away from the centerline plane so that the curved sidewall 407a is located slightly downstream of the curved sidewall 407b so that it is physically not possible for the peg 405 to contact the curved sidewall section wall 407b. Because of this arrangement, contact generally occurs with the oblique sidewall section 397c and simultaneously with the flat sidewall 397b as shown in FIG. 15.

Figure 15:
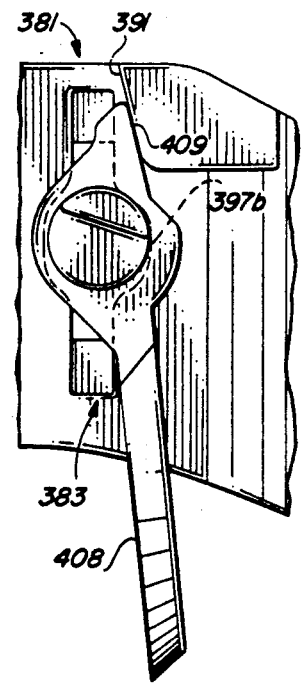
FIGS. 15, 16 and 17 are views similar to FIGS. 10-12 showing a sequence of views as the leaflets translate upstream and rotate to their fully closed position upon reversal of blood flow through the valve having slots as shown in FIG. 13, with FIG. 15 showing the right hand leaflet.

In FIG. 15, the valve is illustrated as showing the peg 405 having contact with the oblique sidewall 397c and also bearing against the flat sidewall 397b that is farther from the valve centerline. In this orientation, the upstream portions 409 of the inflow surfaces of the leaflet side sections 399 are generally in juxtaposition against the camming surfaces 391 of the projections. Thereafter, the further movement of the leaflets is essentially one of rotation, but again the dynamic forces within the bloodstream will determine what will be the precise bearing points for the pegs 405 at any instant and when the contact will shift from the flat sidewall 397a in the open position to the flat sidewall 397b.

Figure 16:
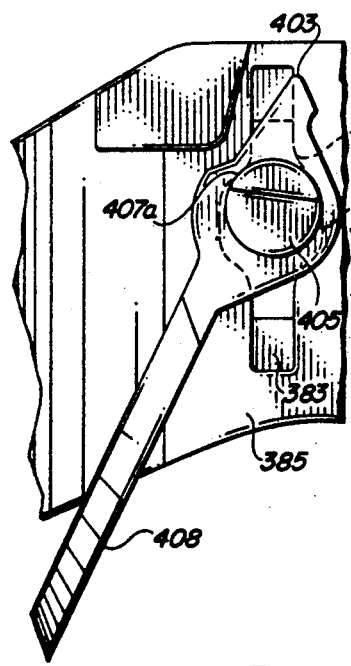

In the view illustrated in FIG. 16, the bloodstream conditions are assumed to be such that the peg 405 has at least momentary bearing contact with the flat sidewall 397a of the central region closest to the centerline plane and with the oblique sidewall section 397c. It is noted that in this orientation, as a result of further rotation of the leaflets, all contact has been lost between the leaflets 401 and the projections 393; thus, further guidance for the continuing closing movement is derived from the interengagement between the pegs 405 and the sidewalls of the slots 383. It can also be seen that the proportions are such that the peg 405 cannot touch either of the curved transition sections 407a, b and will always contact the oblique flat section 397c when at the upstream end of the slot 383.

Figure 17:
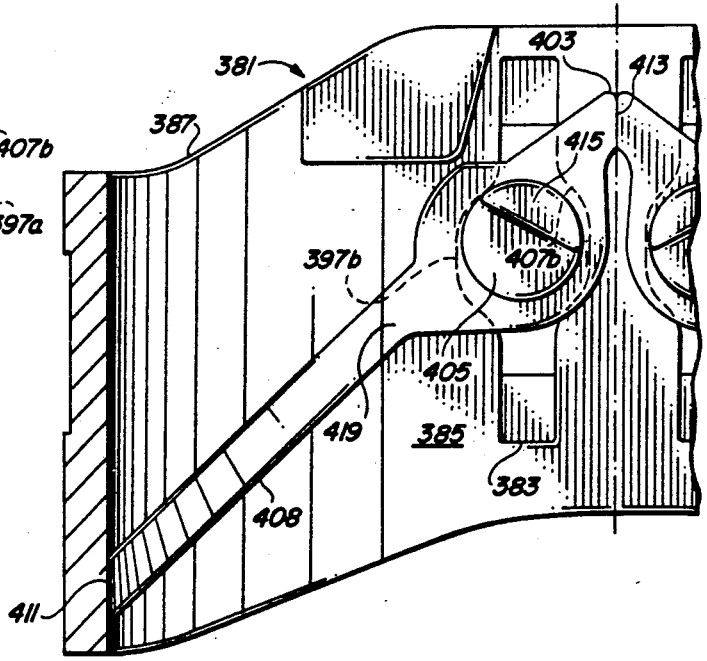

FIG. 17 shows the final, fully closed orientation of the valve 381 wherein the major arcuate edge 411 of the leaflet is in contact with the cylindrical interior sidewall of the valve body 387, and wherein the minor mating edge 413 is abutting and substantially flush against the mating edge surface of the other leaflet, with the plane of abutment being essentially the centerline plane of the valve body. The proportioning and the location of the slots 383 in the flat sidewall sections 385 of the valve body is such that, in the fully closed position, there is preferably contact between the right circular cylindrical wall of the peg 405 and the oblique sidewall 397c of the slot. The major part of the force of the blood against the outflow surface in the closed position is borne by the oblique flat surfaces 397c, and the angular orientation of these surfaces is adjusted so that tight mating contact is assured along the edge surfaces 413. The oblique surfaces 397c are preferably oriented at an angle so as to be within about 10° of parallel to the leaflet flat body sections in the closed position; for example, if the leaflet lies at 45° to the centerline plane in the closed position, the surface 397c might lie at a downstream angle to the centerline plane of between about 35° and about 50°. However, the other factors discussed hereinbefore with respect to the heart valve 301 should be taken into consideration in determining the precise orientation to achieve the desired effect.

In the closed position, there may be little or essentially no leakage flow between the sidewall of the slot 383 lying farther from the centerline and the peg 405 because of the bearing contact with oblique sidewall section 397c. However, so that leakage flow along the base wall of the slots 383 and along the sidewall 397a, will not be greater than desired, as described hereinbefore, the location of the circular sector 415 (which remains on the end surface of the pegs after the size reduction) is oriented so that it provides a flowpath of desired length in this region as best seen in FIG. 17. Moreover, the thickened side sections 399 are proportioned to likewise assure a flow path of appropriate length is present for controlled leakage which would begin in the slots 383 and then proceed between the flat wall sections 385 and the flat lateral edge surfaces 419 of the leaflets, thereby guarding against potentially too great a leakage flow at these locations.

When the flow reverses, the downstream translation and the opening movement of the leaflets 401 in the valve 381 is essentially the same as that in the valve 301 described hereinbefore. One particular advantage of the construction of the valve 381 shown in FIGS. 13 through 17 is the avoidance of the need for maintaining close tolerances on the exterior surfaces of the thickened side sections 399 of the leaflets because the arcuate camming surfaces are not employed, and therefore manufacturing procedures are facilitated.

Although the invention has been described with respect to two preferred embodiments, which include what the inventors presently consider to be the best mode for carrying out the invention, it should be understood that various changes and modifications as would be obvious to one having the ordinary skill in this art may be made without departing from the scope of the invention which is defined by the claims appended hereto. For example, as earlier indicated, the invention is not limited to occluders in the form of pairs of leaflets having flat body sections but is considered to be also applicable to leaflets having curved main body sections that facilitate the creation of a central passageway through the valve of greater area than would a pair of comparably located flat leaflets, which can have advantages in achieving desirable flow patterns, as well as being applicable to valves which employ a single occluder.

By camming contact in this application is meant contact wherein there is relative sliding movement along a surface which is inclined to the centerline plane through the valve body so as to cause pivoting toward the closed position to begin. By a substantial distance as used herein, is meant a distance equal to or greater than the average thickness of the main body portion of the occluder.

Particular features of the invention are emphasized in the claims that follow.

What is claimed is:

1. A prosthetic heart valve including
 a generally annular valve body having an interior wall which defines a central passageway, having a longitudinal axis, for blood flow therethrough,
 occluder means having an inflow surface and an outflow surface, said occluder means being mounted in said valve body to alternate between an open position where the flow of blood therethrough is permitted in a downstream direction generally parallel to said longitudinal axis, and a closed position where the flow of blood in the reverse direction is blocked, said inflow surface facing generally upstream and said outflow surface facing generally downstream with said occluder means in the closed position, and
 a pivot arrangement by which said occluder means is guided in sliding-pivoting movement between said open position and said closed position,
 said pivot arrangement including projection means which extends generally radially inward from said valve body interior wall and is located where a portion of said occluder means lying generally along said inflow surface will slidingly engage said projection means at a first location on said valve body during the closing movement of said occluder means, said pivot arrangement also including interengaging elements on said valve body and on said occluder means, which elements interengage at a second location and cooperate with said projection means in guiding the closing movement of said occluder means, said projection means being positioned so that said sliding engagement between said occluder means and said projection means at said first location is axially upstream of said second location wherein the interengaging contact occurs between said interengaging elements, whereby said sliding engagement between said projection means and said occluder means in combination with said contact between said interengaging elements, as said occluder means is being displaced upstream at the beginning of the reverse flow of blood through said central passageway, is such as to cause said occluder means to immediately begin to pivot about a shifting axis toward said closed position.

2. A prosthetic heart valve according to claim 1 wherein said projection means and said occluder means are proportioned such that, when said occluder means is in the open position and there is abutting contact between said projection means and said inflow surface portion, said location on said occluder means at which such abutting contact occurs is spaced upstream of any pivot axis about which said occluder means will pivot in reaching its fully open position.

3. A prosthetic heart valve according to claim 1 wherein said occluder means includes a pair of flat lateral surfaces parallel to each other which surfaces respectively lie in juxtaposition with two diametrically opposite flat wall sections formed in said interior wall of said annular valve body, and wherein said interengaging means includes depression means located in each said flat wall section and a pair of ear means each having an arcuate surface portion, one of said ear means protruding laterally from each one of said flat lateral surfaces of said occluder means and one of said ear means being received in each depression means.

4. A prosthetic heart valve according to claim 3 wherein each said ear means includes a right circular cylinder of a diameter greater than its axial length.

5. A prosthetic heart valve according to claim 4 wherein said depression means is in the form of groove means which is elongated in a direction generally parallel to said longitudinal axis of said valve body passageway and which has a central section of greater width than a pair of upstream and downstream end sections.

6. A prosthetic heart valve according to claim 5 wherein the width of said central section is not more than about 10 percent greater than the diameter of said right circular cylinder of said ear means, wherein said upstream and downstream end sections are of a width equal to between about 30 and about 60 percent of the width of said central section, and wherein the longitudinal dimension of said central section of said groove is such that the maximum distance said ear means can travel in a straight-line direction is not greater than about 50 percent of the diameter of said right circular cylinder.

7. A prosthetic heart valve according to claim 5 wherein said central section of said groove means has a pair of parallel sidewalls and a base surface which is generally perpendicular to said parallel sidewalls and parallel to said valve body flat wall sections and wherein each said ear means has an outer end face which is relieved to assure a gap exists between said base surface and a downstream portion of the outer end face of said ear means such that said end face will not substantially impede blood flow when said occluder is in the closed position.

8. A prosthetic heart valve according to claim 3 wherein said projection means includes a flat surface which is engaged by an upstream edge portion of said occluder means inflow surface, said flat surface being oriented at an acute downstream angle of between about 5° and about 35° to a plane which is perpendicular to said flat wall sections of said valve body and which includes said longitudinal axis.

9. A prosthetic heart valve according to claim 8 wherein said projection means flat surface terminates in a downstream edge which is engaged by a camming element on the inflow surface of said occluder means to guide subsequent closing movement thereof.

10. A prosthetic heart valve including
a generally annular valve body having an interior, generally arcuate wall which defines a central passageway having a longitudinal axis for blood flow therethrough,
a pair of cooperating occluders, each having an inflow surface and an outflow surface, said occluders being mounted in said valve body to alternate between an open position where the flow of blood in a downstream direction is permitted and a closed position where the flow of blood in the reverse direction is blocked, and
a pivot arrangement by which said occluders are guided in moving between said open position and said closed position,
said pivot arrangement being such as to permit said pair of occluders to assume an orientation substantially parallel to said longitudinal axis in their open position and being such that said occluders are axially displaceable upstream, relative to said valve body, upon the reversal of blood flow, and
said pivot arrangement further being such that first interengaging means is formed on said valve body and said occluders which first interengaging means, upon upstream axial displacement of said occluders, exerts a camming action upon a leading upstream edge portion of each of said occluders, which camming action is effective to cause each said occluder to immediately begin to swing from a substantially parallel open position orientation toward its closed position orientation.

11. A prosthetic heart valve according to claim 10 wherein each occluder has a pair of opposite lateral edges and wherein said pivot arrangement also includes second interengaging means on said valve body and on each said occluder adjacent each lateral edge of each said occluder, said contact at said second interengaging means being between said valve body and regions on each said occluder and being such as to only allow relative translational movement in a direction substantially parallel to said longitudinal axis.

12. A prosthetic heart valve according to claim 11 wherein said second interengaging means includes depression means in said valve body sidewall which receives ear means laterally protruding from said opposite lateral edges of each said occluder.

13. A prosthetic heart valve according to claim 12 wherein said depression means includes open-ended groove means which have centerlines parallel to said valve body longitudinal axis and which have central sections that are asymmetric about said centerlines.

14. A prosthetic heart valve which comprises
an annular valve body having an interior wall which defines a passageway therethrough for the flow of blood in a downstream direction, which passageway has a longitudinal axis,
a pair of leaflets which translate and pivot to alternately open and close said passageway to the flow of blood therethrough,
each of said leaflets having an upstream edge and a pair of coaxial oppositely extending lateral ears, and each said ear has a generally circular cylindrical bearing surface,
said annular valve body interior wall having a pair of diametrically opposed flat wall sections, each of said flat wall sections having formed therein a pair of depression means for respectively receiving one said ear of each of said leaflets,
each said depression means including a central section having a first flat sidewall portion which is perpendicular to said flat wall section of said valve body and generally parallel to said longitudinal axis of said central passageway of said valve body,
said first flat sidewall portion of each depression means facing away from a centerline plane which includes said valve body longitudinal axis and is perpendicular to said valve body flat wall sections,
said valve body also having a plurality of projections which at least in part protrude generally radially inward from said flat wall sections, each of said projections having a camming surface, and
said projections being located so that said camming surfaces are engaged by said leaflets at locations generally along said upstream edges of said leaflets when said leaflets are located in the open position.

15. A heart valve according to claim 14 wherein each said camming surface is a flat surface that faces said centerline plane and is aligned at a downstream angle of between about 5° and about 35° to said centerline plane.

16. A heart valve according to claim 15 wherein each said depression means is in the form of a slot having an axial centerline that is defined by a pair of aligned upstream and downstream terminal sections, wherein said central section of said slot has an opposite second flat sidewall portion which is spaced from and substantially parallel to said first flat sidewall portion, wherein each of said slot terminal sections has a width less than the spacing between said parallel first and second sidewall portions, and wherein said slot also has upstream and downstream curved transition sections located between said central section and each respective terminal section.

17. A heart valve according to claim 16 wherein each said ear includes a right circular cylindrical element having a diameter greater than said width of said terminal sections of said slot and not more than about 10 percent less than said spacing between said first and second parallel sidewall portions.

18. A heart valve according to claim 17 wherein engagement between said upstream curved transition sections and said right circular cylindrical ears assists in guiding the movement of said leaflets as each leaflet pivots to close said passageway.

19. A heart valve according to claim 17 wherein, in the closed position, said upstream edges of said pair of leaflets contact each other and there is no engagement between said ears and said upstream curved transition sections of said slots.

20. A heart valve according to claim 19 wherein said first and second flat sidewall sections of each said slot are parallel to said axial centerline through said slot, wherein said second flat sidewall section is spaced further away from said slot axial centerline than is said first flat sidewall section, and wherein each said slot includes an oblique flat sidewall section which is located between said second flat sidewall section and said upstream curved transition section and against which there is contact by said ear in the closed position.

* * * * *

UNITED STATES PATENT AND TRADEMARK OFFICE
CERTIFICATE OF CORRECTION

PATENT NO. : 5,192,309
DATED : March 9, 1993
INVENTOR(S) : Stupka, et al.

It is certified that error appears in the above-identified patent and that said Letters Patent is hereby corrected as shown below:

Column 7, line 7, "peg" should be --pegs--. Column 11, line 1, after "elements", insert a period (.).

IN THE CLAIMS: Claim 1, column 15, line 15, "wherein" should be --where--.

Signed and Sealed this

Eighteenth Day of January, 1994

Attest:

BRUCE LEHMAN

Attesting Officer

Commissioner of Patents and Trademarks